United States Patent [19]
Yanagawa

[11] Patent Number: 5,908,824
[45] Date of Patent: Jun. 1, 1999

[54] NASALLY ADMINISTRABLE COMPOSITIONS CONTAINING PHYSIOLOGICALLY ACTIVE PEPTIDES

[75] Inventor: Akira Yanagawa, Yokohama, Japan

[73] Assignee: Dott Research Laboratory, Yokohama, Japan

[21] Appl. No.: 08/733,065

[22] Filed: Oct. 16, 1996

[30] Foreign Application Priority Data

| Nov. 1, 1995 | [JP] | Japan | 7-306406 |
| Jan. 17, 1996 | [JP] | Japan | 8-022959 |
| May 28, 1996 | [JP] | Japan | 8-154773 |

[51] Int. Cl.$^6$ .......................... A61K 9/50; A61K 38/03; A61K 38/16

[52] U.S. Cl. ..................... 514/2; 514/3; 514/12; 514/15; 514/53; 514/314; 514/327; 514/510; 514/532; 514/554; 514/675; 530/303; 530/307; 530/313; 530/399; 424/499

[58] Field of Search ................ 514/12, 2, 3, 15, 514/16, 53, 314, 327, 506, 510, 532, 554, 675; 530/303, 307, 313, 399; 424/499

[56] References Cited

U.S. PATENT DOCUMENTS

| 4,613,500 | 9/1986 | Suzuki et al. | 429/85 |
| 5,236,700 | 8/1993 | Koslo et al. | 424/66 |
| 5,578,324 | 11/1996 | Dohi et al. | 424/499 |
| 5,578,567 | 11/1996 | Cardinaux et al. | 514/12 |

FOREIGN PATENT DOCUMENTS

| 0 457 223 | 11/1991 | European Pat. Off. . |
| 0457223 | 11/1991 | European Pat. Off. . |
| 0 635 270 | 1/1995 | European Pat. Off. . |
| 0 681 833 | 11/1995 | European Pat. Off. . |
| 05331071 | 12/1993 | Japan . |
| 89/05645 | 6/1989 | WIPO . |
| 91/04034 | 4/1991 | WIPO . |
| 94/20085 | 9/1994 | WIPO . |
| 94/28020 | 12/1994 | WIPO . |
| WO 9503818 | 2/1995 | WIPO . |

OTHER PUBLICATIONS

Patent Abstracts of Japan, vol. 15, No. 317, Pub. No. JP3120229, Ab. Date Aug. (1991).

Chemical Abstracts, vol. 117, No. 16, Ab. No. 157517, Oct. (1992).

M. Mishima et al., "Promotion of Nasal Absorption of Insulin by Glycyrrhetinic Acid Derivatives", J. Pharmacobio–Dyn., vol. 12, (1989), pp. 31–36.

Budavari et al., "The Merck Index", Merck & Co., (1989).

*Primary Examiner*—Cecilia J. Tsang
*Assistant Examiner*—Anism Gupta
*Attorney, Agent, or Firm*—Foley & Lardner

[57] ABSTRACT

A nasally administrable composition having a physiologically active peptide dispersed homogeneously in and adsorbed homogeneously onto a unique carrier. The composition contains an effective amount of physiologically active peptide dispersed homogeneously in and adsorbed homogeneously onto a mucosa protecting and/or tissue repairing agent, e.g., gefarnate, aceglutamide aluminum, sucralfate, L-glutamine, sofalcone, teprenone, plaunotol, rebamipide, aldioxa, cetraxate or troxipide.

9 Claims, No Drawings

NASALLY ADMINISTRABLE COMPOSITIONS CONTAINING PHYSIOLOGICALLY ACTIVE PEPTIDES

BACKGROUND OF THE INVENTION

1. Field of the Invention

The present invention relates to a nasally administrable composition containing a physiologically active peptide, and, more particularly, to a nasally administrable composition containing a physiologically active peptide such as peptide hormone, physiologically active protein, enzymatic protein and so on with a unique carrier, which is highly absorbable into the body via nasal route.

2. Description of the Prior Art

Physiologically active peptides such as calcitonin, insulin, parathyroid hormone (PTH), human growth hormone (HGH), gonadotropin-releasing hormone (GnRH) and derivatives thereof are polymers which are extensively employed in clinical practice for various medical usage owing to their specific physiological activity.

The physiologically active peptides, however, can little be absorbed intact from the mucous membrane of the intestine because of either being likely to be decomposed with proteases existing in the digestive system or being high in molecular weight and polarity. Hence, the administration method has been limited to injection. However, injection cannot be said to be preferable because it causes pain in patients. In particular, when injection is to be repeated at constant intervals, the patients have to suffer from the pain every time, which may often become too severe to endure. Under the circumstances, there has been strong demand for more simple and convenient means for administering physiologically active peptides, that is, administration via a non-injection route to enable patients to administer the drug by themselves.

As one example of preparations for such non-injection administration, an aerosol in the form of a suspension has been developed for nasal inhalation of calcitonin, in which a fluorinated hydrocarbon is used as a spouting agent. As another means for nasal administration, a spray has been proposed as a nasally administrable liquid preparation, which is a preparation in which calcitonin is formulated with a surface-active agent as an absorption promoter. Furthermore, recently, there have been proposed some nasally administrable powdery preparations with improved absorbability, which are prepared by adsorbing calcitonin onto a polysaccharide such as celluloses. These various techniques for nasal administration, which have recently been actively developed, are said to be in principle superior as a means for administering such physiologically active peptides as unlikely to be administered orally. Since venous plexus develops at the lamina propria mucosae of the nasal cavity, physiologically active peptides, when administered nasally, can be absorbed through the mucous membrane of the nasal cavity into the circulatory system of the body; however, nasally administrable preparations so far proposed cannot be sufficient because of poor absorbability of physiologically active peptides or local irritability, so that they are not commercially available yet.

The inventor of the present invention has actively been studying about carriers for nasal administration of physiologically active peptides such as insulin, calcitonin, parathyroid hormone (PTH), human growth hormone (HGH), gonadotropin-releasing hormone (GnRH) and so on, and has proposed nasally administrable compositions using a polyvalence metal compound such as hydroxyapatite and calcium carbonate as the carrier, finding that water-insoluble substances which are soluble under acidic condition, other than high molecular weight compounds such as polysaccharide celluloses so far studied, can be an desirable carrier for use in nasally administrable physiologically active peptide compositions.

SUMMARY OF THE INVENTION

The present invention has the object to provide a nasally administrable composition that can nasally administer such a physiologically active peptide as unlikely to be administered orally, with higher bioavailability and less irritability than the preparations so far proposed.

Through extensive studies and researches, the inventor of the present invention found that mucosa protecting and/or tissue repairing agents, which had never been used as a carrier for nasally administrable compositions, would be useful as the carrier to administer physiologically active peptides nasally. For example, gastric mucosa protecting and/or tissue repairing agents are soluble under acidic condition, and can promote mucus secretion and alkali secretion, enhance mucous glycoproteins and glycolipids, increase mucous bloodstream and prostaglandin, promote mucous tissular respiration and metabolism, thereby activating the tissues. Also, since these agents are highly adhesive to the mucosa and persist there for a long time, they can provide a long-lasting absorption characteristic. Accordingly, these agents, when administered nasally, are expected to activate the venous plexus of the lamina propria mucosae of the nasal cavity, and therefore, physiologically active peptides, dispersed homogeneously onto the agents as the carrier, are expected to be highly absorbable into the circulatory system of the body through the mucous membrane of the nasal cavity.

The inventor of the present invention actually prepared nasally administrable compositions using a mucosa protecting and/or tissue repairing agent, e.g., a gastric mucosa protecting and/or tissue repairing agent as the carrier, wherein the physiologically active peptide is dispersed homogeneously in and adsorbed homogeneously onto the carrier, and found that the compositions would be highly useful for clinical treatment of patients.

In more detail, the present inventor found that a nasally administrable composition having a physiologically active peptide such as calcitonin, insulin, parathyroid hormone (PTH), human growth hormone (HGH) and gonadotropin-releasing hormone (GnRH) dispersed homogeneously in and adsorbed homogeneously onto the unique carrier, i.e., a mucosa protecting and/or tissue repairing agent, can attain equal or higher bioavailability as compared with that attained by injection.

Furthermore, the present inventor found that the mucosa protecting and/or tissue repairing agent, e.g., a gastric mucosa protecting and/or tissue repairing agent, as the carrier for the nasally administrable composition mentioned above, is also useful for stabilizing the active ingredient of the composition, i.e., a physiologically active peptide.

The present invention has been completed on the basis of these findings.

Accordingly, the present invention provides a nasally administrable composition wherein an effective amount of a physiologically active peptide is dispersed homogeneously in and adsorbed homogeneously onto a mucosa protecting and/or tissue repairing agent, preferably a gastric mucosa protecting and/or tissue repairing agent, as the carrier.

DETAILED DESCRIPTION OF THE INVENTION

It should be noted herein that mucosa protecting and/or tissue repairing agents had never been expected to be a carrier for a nasally administrable composition, and the present inventor is the first to have discovered the applicability.

In the present invention, gastric mucosa protecting and/or tissue repairing agents are most preferable as the carrier. Such agents include gefarnate (trade name: Gefanil), aceglutamide aluminum (trade name: Glumal), sucralfate (trade name: Ulcerlmin), L-glutamine (trade name: Glumin), sofalcone (trade name: Solon), teprenone (trade name: Selbex), plaunotol (trade name: Kelnac), rebamipide (trade name: Mucosta), aldioxa (trade name: Altanta, Isalon, Ascomp, etc.), cetraxate (trade name: Neuer), and troxipide (trade name: Aplace). The present inventor prepared nasally administrable compositions by homogeneously dispersing physiologically active peptides onto the above-mentioned agents and found that the compositions thereby prepared were highly absorbable into the body through nasal mucous membrane.

Phygiologically active peptides to be used as the active ingredient of the composition according to the present invention may be peptide hormones, physiologically active proteins, enzymatic proteins, opioid peptides, and so on.

Examples of such physiologically active peptides include parathyroid hormone (PTH), calcitonin, insulin, angiotensin, glucagon, gastorin, secretin, growth hormone (GH), human growth hormone (HGH), prolactin (luteotropic hormone), gonadotropin (gonodotropic hormone), thyrotropic hormone, adrenocorticotropic hormone, melanocyte stimulating hormone, vasopressine, oxytocin, protirelin, luteinizing hormone (LH), corticotropin, somatropin, thyrotropin (thyroid stimulating hormone), somatostatin (growth hormone inhibiting factor), gonadotropin-releasing hormone (GnRH) and derivatives thereof, opioid peptides such as endorphins and enkephalins, G-CSF, erythropoietin, superoxide dismutase (SOD), interferon, interleukin, urokinase, lysozyme, vaccine and so on.

It is to be noted herein that the physiologically active peptides to be used for the present invention are not limited to the above examples and that any nasally administrable physiologically active peptide may be formulated into the composition according to the present invention.

Among those physiologically active peptides as described above, peptide hormones such as calcitonin, insulin and somatostatin are preferred. In particular, calcitonin, insulin, parathyroid hormone (PTH), human growth hormone (HGH) and gonadotropin-releasing hormone (GnRH) are preferred.

Examples of calcitonin include salmon calcitonin, human calcitonin, salmon/human chimera calcitonin, hog calcitonin, chicken calcitonin, cattle calcitonin, eel calcitonin, and so on. These calcitonins are naturally-occurring, extractable ones that are commercially available. It can be noted herein that eel calcitonin is higher in stability than human calcitonin that in turn is higher than salmon calcitonin; however, even the salmon calcitonin that is relatively low in stability, when dispersed homogeneously in and adsorbed homogeneously onto the unique carrier of the present invention, was found to show high bioavailability and high concentration in the blood. Hence, every commercially available calcitonin is suitable for use in the composition of the present invention.

Therefore, a preferable mode of the present invention is a nasally administrable composition in which an effective amount of calcitonin is dispersed homogeneously in and adsorbed homogeneously onto a gastric mucosa protecting and/or tissue repairing agent such as gefarnate, aceglutamide aluminum, sucralfate, L-glutamine, sofalcone, teprenone, plaunotol, rebamipide, aldioxa, cetraxate and troxipide.

Another preferable mode of the present invention is a nasally administrable composition in which an effective amount of parathyroid hormone (PTH) is dispersed homogeneously in and adsorbed homogeneously onto a gastric mucosa protecting and/or tissue repairing agent such as gefarnate, aceglutamide aluminum, sucralfate, L-glutamine, sofalcone, teprenone, plaunotol, rebamipide, aldioxa, cetraxate and troxipide.

Examples of parathyroid hormone (PTH) for use in this composition include human PTH, cattle PTH, hog PTH and so on, among which human PTH is most preferable.

A further preferable mode of the present invention is a nasally administrable composition in which an effective amount of gonadotropin-releasing hormone (GnRH) to promote LH secretion is dispersed homogeneously in and adsorbed homogeneously onto a gastric mucosa protecting and/or tissue repairing agent such as gefarnate, aceglutamide aluminum, sucralfate, L-glutamine, sofalcone, teprenone, plaunotol, rebamipide, aldioxa, cetraxate and troxipide.

Preferable GnRH for use in this composition is a derivative administrable to human, for example, buserelin acetate.

Still another preferable mode of the present invention is a nasally administrable composition in which an effective amount of growth hormone (GH), preferably human growth hormone (HGH), is dispersed homogeneously in and adsorbed homogeneously onto a gastric mucosa protecting and/or tissue repairing agent such as gefarnate, aceglutamide aluminum, sucralfate, L-glutamine, sofalcone, teprenone, plaunotol, rebamipide, aldioxa, cetraxate and troxipide.

The amount of the above-mentioned physiologically active peptides to be contained in the composition of the present invention may vary with the individual active ingredient to be chosen (for example, with a relative activity strength of calcitonin, an insulin unit, etc.), the disease to be treated, desired number of administration, desired effect of therapy, and so on. Thus, when administering the composition of the present invention, i.e., via the nasal route, the amount of the physiologically active peptide to be administered can be determined on the basis of a comparison with other known preparations cantaining the same in terms of bioavailability.

For example, when insulin is administered subcutaneously to treat a diabetic patient, an initial dose is usually 4–20 insulin units at one time, a maintenance dose is usually 4–100 insulin units per day, and a maximum dose is usually 800 insulin units per day. Accordingly, when nasally administering insulin in the composition according to the present invention, it is appropriate to use 4–100 insulin units.

And, when calcitonin, e.g. salmon calcitonin, is administered intramuscularly, a dose of about 50–100 MRC units (IU) is used once/day to three times/week. Accordingly, when nasally administering calcitonin in the composition of present invention, it is appropriate to use 50–400 MRC units (IU), preferably 100–200 MRC units (IU) to be administered once/day to three times/week.

For nasal administration, it is convenient to administer the required dose as mentioned above at one time, that is, to administer nasally 50–400 MRC units, preferably 100–200 units, of calcitonin at one time.

Therefore, when preparing the composition of the present invention, it is appropriate to have the physiologically active peptide contained at a rate of from 0.005% to 30%, preferably from 0.01% to 20%, more preferably from 0.1% to 5.0%, per the 100% total weight of the preparation.

On the other hand, the composition of the present invention can achieve higher nasal absorbability when it contains a mucosa protecting and/or tissue repairing agent, e.g., a gastric mucosa protecting and/or tissue repairing agent as the carrier at a rate of from 70%–99.995%, preferably from 80–99.99%, more preferably from 95%–99.9%, per the 100% total weight of the prepartion.

The physiologically active peptide composition of the present invention is prepared by admixing the physiologically active peptide with the carrier, i.e., a mucosa protecting and/or tissue repairing agent, preferably a gastric mucosa protecting and/or tissue repairing agent. As an example of preparation, a gastric mucosa protecting and/or tissue repairing agent such as sucralfate is mixed with a low substituted hydroxypropylcellulose under stirring, then left for 5 minutes. To the mixture a physiologically active peptide such as calcitonin is added and further mixed. After adding a small amount of purified water, the resulting mixture is kneaded and freeze-dried at −40° C. over 10–14 hours, and then warmed to 30° C. over 3–5 hours, preferably over 4 hours. Then magnesium stearate is added and the mixture is homogeneously pulverized in a mortar, thereby yielding a fine powder (nasally administrable composition) wherein a physiologically active peptide is dispersed homogeneously in and adsorbed homogeneously onto a mucosa protecting and/or tissue repairing agent. The amount of each ingredient to be contained is not specifically limited; however, for example, the amount of calcitonin can be 200 IU/30 mg as a composition, that of PTH (1–34) can be 60 µg/30 mg or 90 µg/40 mg as a composition, and that of GnRH can be 50 µg/30 mg as a composition.

In order to prevent loss of the activity of the physiologically active peptide prior to administration, the composition may be filled in capsules of a low-grease type and packaged in an appropriate form, preferably in a closed form, by combining blister packing with aluminum packaging.

Gastric mucosa protecting and/or tissue repairing agents other than sucralfate, i.e., aldioxa, cetraxate and so on can be likewise treated in substantially the same manner as described above to thereby yield the compositions of the present invention.

The following Test Examples show the specific effects offered by the compositions of the present invention.

TEST EXAMPLE 1

A nasally administrable composition of the present invention was prepared by using insulin as the physiologically active peptide and sucralfate (trade name: Ulcerlmin) as the carrier.

The composition contained insulin at 2.4 mg/rabbit (5 insulin units (IU)/rabbit).

The composition was nasally administered to six male New Zealand rabbits at one time, and the average fall of the blood sugar was measured at 0, 15, 30, 60, 120 and 180 min after administration.

For comparison, 2 IU/rabbit of insulin was subcutaneously injected to six male New Zealand rabbits and the average fall of the blood sugar was measured at 0, 60, 120, 240, and 360 min after administration.

The results are shown in Table 1, in which the average fall of the blood sugar is indicated in percentage assuming the blood sugar level at 0 min to be 100%.

TABLE 1

| Average fall of the blood sugar | | | | | | |
| --- | --- | --- | --- | --- | --- | --- |
| Composition of the present invention | Time after administration (min) | | | | | |
| | 0 | 15 | 30 | 60 | 120 | 180 |
| | 100% | 98% | 62% | 68% | 74% | 81% |
| Control | Time after administration (min) | | | | | |
| | 0 | 60 | 120 | 240 | 360 | |
| | 100% | 57% | 56% | 84% | 94% | |

As is apparent from Table 1 above, the composition of the present invention greatly decreased the blood sugar, which suggests that sucralfate as the carrier was effective to attain a high extent of absorption of insulin through nasal route.

TEST EXAMPLE 2

A nasally administrable composition of the present invention was prepared by using salmon calcitonin as the physiologically active peptide and sucralfate (trade name: Ulcerlmin) as the carrier. Salmon calcitonin was contained at 200 MRC (IU)/30 mg.

The composition was nasally administered to two healthy male adults at one time, and 2.5 ml blood sample was collected from each subject at 0, 5, 10, 15, 20, 30, 45, 60, 90, 120 and 180 min after administration. The concentration of salmon calcitonin in each blood sample was assayed with a standard RIA assay kit.

The results are shown in Table 2 below.

TABLE 2

| Sampling time (min) | Concentration of salmon calcitonin in the blood (pg/ml) | |
|---|---|---|
| | Subject Nos. | |
| | No. 1 | No. 2 |
| 0 | ~7 | ~7 |
| 5 | 106.28 | 98.86 |
| 10 | 120.62 | 110.68 |
| 15 | 110.69 | 124.54 |
| 20 | 104.52 | 130.25 |
| 30 | 84.61 | 105.38 |
| 45 | 94.54 | 98.43 |
| 60 | 91.55 | 95.28 |
| 90 | 78.13 | 80.62 |
| 120 | 58.42 | 60.58 |
| 180 | 45.91 | 67.21 |

As is apparent from Table 2 above, the composition of the present invention using sucralfate (trade name: Ulcerlmin) as the carrier attained a high degree of absorption of salmon calcitonin into the blood through nasal route.

TEST EXAMPLE 3

A nasally administrable composition of the present invention was prepared by using salmon calcitonin as the physiologically active peptide and aldioxa (trade name: Alanta) as the carrier. Salmon calcitonin was contained at 200 MRC (IU)/30 mg.

The composition was nasally administered to two healthy male adults at one time, and 2.5 ml blood sample was collected from each subject at 0, 5, 10, 15, 20, 30, 45, 60, 90, 120 and 180 min after administration. The concentration of salmon calcitonin in each blood sample was assayed with a standard RIA assay kit.

The results are shown in Table 3 below.

TABLE 3

| Sampling time (min) | Concentration of salmon calcitonin in the blood (pg/ml) | |
|---|---|---|
| | Subject Nos. | |
| | No. 3 | No. 4 |
| 0 | ~7 | ~7 |
| 5 | 82.6 | 78.25 |
| 10 | 93.45 | 106.67 |
| 15 | 72.65 | 119.26 |
| 20 | 49.85 | 95.07 |
| 30 | 77.03 | 106.42 |
| 45 | 62.04 | 60.68 |
| 60 | 42.79 | 102.78 |
| 90 | 12.54 | 42.97 |
| 120 | ~7 | ~7 |
| 180 | ~7 | ~7 |

As is apparent from Table 3 above, the composition of the present invention using aldioxa (trade name: Alanta) as the carrier attained a high degree of absorption of salmon calcitonin into the blood through nasal route.

TEST EXAMPLE 4

A nasally administrable composition of the present invention was prepared by using PTH (1-34) as the physiologically active peptide and sucralfate (trade name: Ulcerlmin) as the carrier. PTH (1-34) was contained at 60 $\mu$g/30 mg.

The composition was nasally administered to six healthy male adults (Subject Nos. 5–10) at one time, and 2.5 ml blood sample was collected from each subject at 0, 5, 10, 15, 20, 30, 45, 60, 90, 120, 150 and 180 min after administration. The concentration of PTH (1-34) in each blood sample was assayed by ELISA 1-34 PTH 2 antibody method.

The results are shown in Tables 4 and 5 below.

TABLE 4

| Sampling time (min) | Concentration of PTH (1–34) in the blood (pg/ml) | | |
|---|---|---|---|
| | Subject Nos. | | |
| | No. 5 | No. 6 | No. 7 |
| 0 | ~10 | 10.6 | 11.2 |
| 5 | 63.1 | 36.3 | 54.2 |
| 10 | 61.0 | 41.3 | 70.9 |
| 15 | 23.6 | 41.2 | 49.6 |
| 20 | 16.2 | 34.7 | 39.3 |
| 30 | 13.1 | 38.0 | 28.5 |
| 45 | 11.4 | 37.3 | 23.0 |
| 60 | 15.4 | 33.9 | 20.5 |
| 90 | ~10 | 36.0 | 17.8 |
| 120 | ~10 | 35.1 | 16.4 |
| 150 | ~10 | 35.0 | 14.3 |
| 180 | ~10 | 30.9 | 12.2 |

TABLE 5

| Sampling time (min) | Concentration of PTH (1–34) in the blood (pg/ml) | | |
|---|---|---|---|
| | Subject Nos. | | |
| | No. 8 | No. 9 | No. 10 |
| 0 | ~10 | ~10 | ~10 |
| 5 | 20.6 | 57.1 | 40.6 |
| 10 | 20.3 | 51.6 | 52.5 |
| 15 | 18.4 | 42.7 | 45.8 |
| 20 | 19.2 | 29.7 | 36.6 |
| 30 | 18.4 | 23.2 | 29.5 |
| 45 | 18.8 | 18.0 | 22.4 |
| 60 | 16.2 | 13.3 | 16.7 |
| 90 | 13.4 | 12.1 | 13.1 |
| 120 | 13.1 | 12.4 | 11.2 |
| 150 | 14.0 | ~10 | 11.4 |
| 180 | 11.8 | ~10 | ~10 |

As is apparent from Tables 4 and 5 above, the composition of the present invention using sucralfate (trade name: Ulcerlmin) as the carrier attained a high degree of absorption of PTH (1-34) into the blood through nasal route.

TEST EXAMPLE 5

A nasally administrable composition of the present invention was prepared by using PTH (1-34) as the physiologically active peptide and sofalcone (trade name: Solon) as the carrier. PTH (1-34) was contained at 60 g g/30 mg.

The composition was nasally administered to six healthy male adults (Subject Nos. 11–16) at one time, and 2.5 ml blood sample was collected from each subject at 0, 5, 10, 15, 20, 30, 45, 60, 90, 120, 150 and 180 min after administration. The concentration of PTH (1-34) in each blood sample was assayed with a PTH kit.

The results are shown in Tables 6 and 7 below.

TABLE 6

| Sampling time (min) | Concentration of PTH (1–34) in the blood (pg/ml) Subject Nos. | | |
|---|---|---|---|
| | No. 11 | No. 12 | No. 13 |
| 0   | 25.1 | 16.7 | 14.9 |
| 5   | 30.5 | 27.6 | 28.2 |
| 10  | 33.3 | 29.8 | 37.5 |
| 15  | 33.5 | 29.9 | 33.1 |
| 20  | 30.5 | 31.4 | 30.5 |
| 30  | 31.0 | 33.1 | 29.9 |
| 45  | 28.3 | 30.2 | 24.9 |
| 60  | 27.3 | 27.1 | 23.4 |
| 90  | 25.8 | 22.6 | 21.8 |
| 120 | 23.7 | 22.2 | 20.5 |
| 150 | 22.3 | 19.0 | 18.8 |
| 180 | 22.7 | 20.5 | 17.9 |

TABLE 7

| Sampling time (min) | Concentration of PTH (1–34) in the blood (pg/ml) Subject Nos. | | |
|---|---|---|---|
| | No. 14 | No. 15 | No. 16 |
| 0   | 15.7 | 11.1 | 14.7 |
| 5   | 24.4 | 61.1 | 40.5 |
| 10  | 26.8 | 70.2 | 29.6 |
| 15  | 26.8 | 56.4 | 30.0 |
| 20  | 26.7 | 44.0 | 21.2 |
| 30  | 25.9 | 22.0 | 17.0 |
| 45  | 28.4 | 17.6 | 17.8 |
| 60  | 27.0 | 14.8 | 16.0 |
| 90  | 29.7 | 15.3 | 14.9 |
| 120 | 25.5 | 9.5  | 14.5 |
| 150 | 20.8 | 14.0 | 16.2 |
| 180 | 20.2 | 12.2 | 13.3 |

As is apparent from Tables 6 and 7 above, the composition of the present invention using sofalcone (trade name: Solon) as the carrier attained a high degree of absorption of PTH (1-34) into the blood through nasal route.

TEST EXAMPLE 6

A nasally administrable composition of the present invention was prepared by using a derivative of gonadotropin-releasing hormone (GnRH), i.e., buserelin acetate as the physiologically active peptide and sucralfate (trade name: Ulcerlmin) as the carrier. Buserelin acetate was contained at 50 μg/30 mg.

The composition was nasally administered to two healthy male adults (Subject Nos. 17 and 18) at one time, and 2.5 ml blood sample was collected from each subject at 0, 5, 10, 15, 20, 30, 45, 60, 90, 120 and 240 min after administration. The concentration of buserelin in each blood sample was assayed by direct method.

The results are shown in Table 8 below.

TABLE 8

| Sampling time (min) | Concentration of buserelin in the blood (pg/ml) Subject Nos. | |
|---|---|---|
| | No. 17 | No. 18 |
| 0   | ~30 | ~30 |
| 5   | 124 | 52  |
| 10  | 271 | 133 |
| 15  | 330 | 172 |
| 20  | 438 | 204 |
| 30  | 454 | 119 |
| 45  | 336 | 96  |
| 60  | 299 | 81  |
| 90  | 188 | 55  |
| 120 | 144 | 52  |
| 240 | 72  | ~30 |

As is apparent from Table 8 above, the composition of the present invention using sucralfate (trade name: Ulcerlmin) as the carrier attained a high degree of absorption of GnRH into the blood through nasal route.

TEST EXAMPLE 7

A nasally administrable composition of the present invention was prepared by using PTH (1-34) as the physiologically active peptide and sucralfate (trade name: Ulcerlmin) as the carrier. PTH (1-34) was contained at 90 μg/40 mg.

The composition was nasally administered to six healthy male adults (Subject Nos. 19–24) at one time, and 2.5 ml blood sample was collected from each subject at 0, 5, 10, 15, 20, 30, 45, 60, 90, 120, 180, 240 and 360 min after administration. The concentration of PTH (1-34) in each blood sample was assayed by ELISA 1-34 PTH 2 antibody method.

The results are shown in Tables 9 and 10 below.

TABLE 9

| Sampling time (min) | Concentration of PTH (1–34) in the blood (pg/ml) Subject Nos. | | |
|---|---|---|---|
| | No. 19 | No. 20 | No. 21 |
| 0   | 0  | 0   | 0   |
| 5   | 0  | 31  | 67  |
| 10  | 0  | 24  | 69  |
| 15  | 37 | 0   | 52  |
| 20  | 12 | 33  | 73  |
| 30  | 10 | 27  | 134 |
| 45  | 0  | 29  | 46  |
| 60  | 23 | 265 | 60  |
| 90  | 19 | 21  | 143 |
| 120 | 0  | 29  | 46  |
| 180 | 0  | 32  | 39  |
| 240 | 0  | 18  | 0   |
| 360 | 0  | 11  | 0   |

TABLE 10

| Sampling time (min) | Concentration of PTH (1–34) in the blood (pg/ml) Subject Nos. | | |
|---|---|---|---|
| | No. 22 | No. 23 | No. 24 |
| 0 | 0 | 0 | 0 |
| 5 | 0 | 22 | 46 |
| 10 | 24 | 16 | 11 |
| 15 | 13 | 25 | 24 |
| 20 | 18 | 37 | 504 |
| 30 | 0 | 14 | 0 |
| 45 | 0 | 0 | 0 |
| 60 | 14 | 11 | 0 |
| 90 | 47 | 0 | 0 |
| 120 | 0 | 12 | 0 |
| 180 | 0 | 0 | 0 |
| 240 | 31 | 0 | 0 |
| 360 | 0 | 0 | 0 |

As is apparent from Tables 9 and 10 above, the composition of the present invention using sucralfate (trade name: Ulcerlmin) as the carrier attained a high degree of absorption of PTH (1-34) into the blood through nasal route.

TEST EXAMPLE 8

Nasally administrable compositions of the present invention were prepared by using human growth hormone (HGH) as the physiologically active peptide and sucralfate (trade name: Ulcerlmin) or sofalcone (trade name: Solon) as the carrier. A 1000 mg composition contained 150 mg HGH. The compositions were nasally administered at one time to six healthy male adults (Subject Nos. 25–30), of whom three were given the composition comprising 6.825 unit HGH and 25 mg sucralfate, and the other three were given the composition comprising 6.825 unit HGH and 25 mg sofalcone. From each subject 2.5 ml blood sample was collected at 0, 5, 10, 15, 20, 30, 45, 60, 90, 120 and 180 min after administration, and the HGH concentration in each blood sample was assayed with an assay kit based on IRMA (immunoradiometric assay method) using solid phase assay method.

The results are shown in Table 11 (carrier: sucralfate) and Table 12 (carrier: sofalcone) below.

TABLE 11

| Carrier | Concentration of HGH in the blood (ng/ml) Sucralfate | | |
|---|---|---|---|
| Sampling time (min) | Subject Nos. | | |
| | No. 25 | No. 26 | No. 27 |
| 0 | 0.5 | 0.7 | 1.0 |
| 5 | 0.5 | 3.0 | 4.5 |
| 10 | 0.8 | 3.7 | 5.1 |
| 15 | 1.3 | 3.5 | 6.5 |
| 20 | 1.9 | 3.6 | 7.3 |
| 30 | 6.1 | 3.3 | 7.4 |
| 45 | 23.1 | 2.5 | 10.2 |
| 60 | 20.8 | 2.0 | 12.8 |
| 90 | 6.4 | 1.3 | 4.7 |
| 120 | 2.6 | 1.0 | 1.8 |
| 180 | 0.8 | 0.7 | 0.7 |

TABLE 12

| Carrier | Concentration of HGH in the blood (ng/ml) Sofalcone | | |
|---|---|---|---|
| Sampling time (min) | Subject Nos. | | |
| | No. 28 | No. 29 | No. 30 |
| 0 | 0.2 | 0.1 | 1.5 |
| 5 | 0.5 | 1.7 | 5.8 |
| 10 | 0.7 | 2.8 | 5.2 |
| 15 | 0.9 | 3.5 | 4.9 |
| 20 | 0.8 | 3.6 | 3.9 |
| 30 | 1.0 | 4.0 | 3.5 |
| 45 | 2.2 | 3.4 | 2.3 |
| 60 | 1.2 | 2.4 | 1.4 |
| 90 | 0.8 | 1.2 | 0.7 |
| 120 | 0.5 | 0.8 | 0.4 |
| 180 | 0.3 | 0.5 | 0.3 |

As is apparent from Tables 11 and 12 above, the composition of the present invention using either sucralfate or sofalcone as the carrier attained a high degree of absorption of HGH into the blood through nasal route.

TEST EXAMPLE 9

A nasally administrable composition of the present invention was prepared by using β-endorphin as the physiologically active peptide and sucralfate (trade name: Ulcerlmin) as the carrier. β-endorphin was contained at 3 μg/30 mg. The composition was nasally administered to two rhesus monkeys weighing about 5 kg. The blood sample was collected from each of the monkeys at 0, 5, 10, 15, 20 and 30 min after administration, and the concentration of β-endorphin in each blood sample was assayed.

The results are shown in Table 13.

TABLE 13

| Sampling time (min) | Concentration of β-endorphin in the blood (pg/ml) | |
|---|---|---|
| | Monkey No. 1 | Monkey No. 2 |
| 0 | 44 | 44 |
| 5 | 48 | 62 |
| 10 | 58 | 60 |
| 15 | 60 | 56 |
| 20 | 84 | 58 |
| 30 | 96 | 48 |

As is apparent from Table 13 above, the composition of the present invention using sucralfate as the carrier attained a high degree of absorption of β-endorphin into the blood through nasal route.

TEST EXAMPLE 10

A nasally administrable composition of the present invention was prepared by using salmon calcitonin as the physiologically active peptide and sucralfate (trade name: Ulcerlmin) as the carrier. Salmon calcitonin was contained at 200 MRC (IU)/30 mg.

The composition was nasally administered to two healthy male adults (Subject Nos. 31 and 32) at one time, and 2.5 ml blood sample was collected from each subject at 0, 5, 10, 15, 20, 30, 45, 60, 90, 120, 180 and 240 min after administration. The concentration of salmon calcitonin in each blood sample was assayed with a standard RIA kit, and the results are shown in Table 14.

Also, change in $Ca^{2+}$ concentration in the blood was bioassayed and the results are shown in Table 15.

On the other hand, when calcitonin concentration in the blood increases, parathyroid hormone (PTH) is released in order to increase $Ca^{2+}$ in the blood, that is an antagonistic reaction to the hypocalcemic effect of calcitonin. Accordingly, the concentration of intact PTH (1-84) in the blood was measured and the results are shown in Table 16.

TABLE 14

|  | Concentration of salmon calcitonin in the blood (pg/ml) | |
|---|---|---|
| Sampling | Subject Nos. | |
| time (min) | No. 31 | No. 32 |
| 0 | 0 | 0 |
| 5 | 66 | 90 |
| 10 | 112 | 302 |
| 15 | 90 | 346 |
| 20 | 94 | 295 |
| 30 | 90 | 154 |
| 45 | 64 | 65 |
| 60 | 58 | 52 |
| 90 | 54 | 41 |
| 120 | 44 | 11 |
| 180 | 43 | 20 |
| 240 | 36 | <5 |

TABLE 15

|  | Change in $Ca^{2+}$ concentration in the blood | | |
|---|---|---|---|
| Sampling | Subject Nos. | | |
| time (min) | No. 31 | No. 32 | Average |
| 0 | 1.32 | 1.32 | 1.32 |
| 5 | 1.32 | 1.30 | 1.31 |
| 10 | 1.28 | 1.27 | 1.275 |
| 15 | 1.30 | 1.28 | 1.29 |
| 20 | 1.30 | 1.30 | 1.30 |
| 30 | 1.26 | 1.23 | 1.245 |
| 45 | 1.25 | 1.29 | 1.27 |
| 60 | 1.26 | 1.26 | 1.26 |
| 90 | 1.26 | 1.25 | 1.255 |
| 120 | 1.31 | 1.26 | 1.285 |
| 180 | 1.26 | 1.21 | 1.235 |
| 240 | 1.25 | 1.21 | 1.23 |

TABLE 16

|  | Concentration of intact PTH (1–84) in the blood (pg/ml) | |
|---|---|---|
| Sampling | Subject Nos. | |
| time (min) | No. 31 | No. 32 |
| 0 | 25 | 35 |
| 5 | 29 | 35 |
| 10 | 24 | 35 |
| 15 | 29 | 39 |
| 20 | 28 | 38 |
| 30 | 34 | 43 |
| 45 | 42 | 42 |
| 60 | 27 | 45 |
| 90 | 33 | 44 |
| 120 | 40 | 47 |
| 180 | 47 | 48 |
| 240 | 58 | 62 |

Tables 14 through 16 above show that the composition of the present invention using sucralfate as the carrier attained a high degree of absorption of salmon calcitonin into the blood, as supported by the bioassay data on the change in $Ca^{2}+$ concentration in the blood and the increase in intact PTH (1-84).

It can be said that these effects obtained are characteristic to the present invention.

Similar results were obtained with other physiologically active peptides combined with a gastric mucosa protecting and/or tissue repairing agents such as sucralfate (trade name: Ulcerlmin), sofalcone (trade name: Solon), cetraxate (trade name: Neuer), rebamipide (trade name: Mucosta), aldioxa (trade name: Alanta, Isalon, etc.) and so on.

TEST EXAMPLE 11 (Stabilization test)

A nasally administrable composition of the present invention was prepared by using salmon calcitonin as the physiologically active peptide and sucralfate (trade name: Ulcerlmin) as the carrier.

The composition was filled in a capsule, which was left under a severe condition of 40° C. to observe the change in the amount of salmon calcitonin contained in the composition at 1, 2, 3, 4 and 8 weeks thereafter.

The amount of salmon calcitonin initially contained was 220–245 MRC (IU)/30 mg capsule.

A salmon calcitonin composition using calcium carbonate as the carrier was also tested for comparison.

The results are shown in Table 17 below.

TABLE 17

Change in the amount of salmon calcitonin in the composition
(IU/capsule)

| | Carrier | | | | | | |
|---|---|---|---|---|---|---|---|
| | Sucralfate | | | | Calcium carbonate | | |
| | Sample No. 1 | Sample No. 2 | Sample No. 3 | Average | Sample No. 1 | Sample No. 2 | Sample No. 3 | Average |
| Initial | 221 | 227 | 227 | 225.05 | 232 | 237 | 235 | 231.00 |
| Week 1 | 185 | 159 | 184 | 176.00 | 128 | 125 | 153 | 135.55 |
| Week 2 | 155 | 155 | 155 | 155.00 | 81 | 74 | 80 | 78.28 |
| Week 3 | 158 | 156 | 158 | 157.23 | 41 | 44 | 39 | 41.49 |
| Week 4 | 149 | 150 | 141 | 146.90 | 31 | 35 | 33 | 33.14 |
| Week 8 | 141 | 146 | 133 | 140.00 | 16 | 21 | 25 | 26.67 |

As is apparent from Table 17 above, sucralfate (trade name: Ulcerlmin) was found to stabilize salmon calcitonin under the severe condition of 40° C., whereas calcium carbonate did not show such an stabilizing effect on salmon calcitonin under the same condition.

By testing likewise, it was found that other physiologically active peptides were also stabilized by gastric mucosa protecting and/or tissue repairing agents such as sucralfate (trade name: Ulcerlmin), sofalcone (trade name: Solon), cetraxate (trade name: Neuer), rebamipide (trade name: Mucosta) and aldioxa (trade name: Alanta, Isalon, etc.).

The following are the examples of the composition according to the present invention, which, however, are non-limiting.

Powdery Composition 1

A calcitonin composition was prepared from the following ingredients:

| | | |
|---|---|---|
| Calcitonin | 6540 | IU |
| Magnesium stearate | 60 | mg |
| HPC-L | 20 | mg |
| Sucralfate | the rest part | |
| (or Aldioxa) | | |
| | 1000 | mg |

Powdery Composition 2

A PTH (1-34) composition was prepared from the following ingredients:

| | | |
|---|---|---|
| PTH (1–34) | 1962 | μg |
| Magnesium stearate | 60 | mg |
| HPC-L | 20 | mg |
| Sofalcone | the rest part | |
| (or Sucralfate) | | |
| | 1000 | mg |

As described hereinabove, the present invention allows nasal administration of physiologically active peptides which are unlikely or difficult to be orally administered, with high absorbability and without irritability, which provides an effective therapy for patients.

The present invention would therefore be of great use in clinical practice.

What is claimed is:

1. A nasally administrable composition containing a physiologically active peptide, wherein an effective amount of the physiologically active peptide is dispersed homogeneously in and adsorbed homogeneously onto one or more gastric mucosa protecting or gastric mucosa tissue repairing agents selected from the group consisting of gefarnate, aceglutamide aluminum, sucralfate, L-glutamine, sofalcone, teprenone, plaunotol, rebamipide, aldioxa, and troxipide.

2. A nasally administrable composition according to claim 1 wherein the physiologically active peptide is a peptide hormone, a physiologically active protein, an enzymatic protein, or an opioid peptide.

3. A nasally administrable composition according to claim 1 wherein the physiologically active peptide is calcitonin, insulin, parathyroid hormone, human growth hormone, gonadotropin-releasing hormone or a derivative thereof.

4. A nasally administrable composition wherein calcitonin is dispersed homogeneously in and adsorbed homogeneously onto one or more gastric mucosa protecting or gastric mucosa tissue repairing agents selected from the group consisting of gefarnate, aceglutamide aluminum, sucralfate, L-glutamine, sofalcone, teprenone, plaunotol, rebamipide, aldioxa, and troxipide.

5. A nasally administrable composition wherein parathyroid hormone is dispersed homogeneously in and adsorbed homogeneously onto one or more gastric mucosa protecting or gastric mucosa tissue repairing agents selected from the group consisting of gefarnate, aceglutamide aluminum, sucralfate, L-glutamine, sofalcone, teprenone, plaunotol, rebamipide, aldioxa, and troxipide.

6. A nasally administrable composition wherein gonadotropin-releasing hormone is dispersed homogeneously in and adsorbed homogeneously onto one or more gastric mucosa protecting or gastric mucosa tissue repairing agents selected form the group consisting of gefarnate, aceglutamide aluminum, sucralfate, L-glutanine, sofalcone, teprenone, plaunotol, rebamipide, aldioxa, and troxipide.

7. A nasally administrable composition wherein human growth hormone is dispersed homogeneously in and adsorbed homogeneously onto one or more gastric mucosa protecting or gastric mucosa tissue repairing agents selected from the group consisting of gefarnate, aceglutamide aluminum, sucralfate, L-glutamine, sofalcone, teprenone, plaunotol, rebamipide, aldioxa, and troxipide.

8. A method of stabilizing a physiologically active peptide, comprising combining the physiologically active peptide with one or more gastric mucosa protecting or gastric mucosa tissue repairing agents selected from the group consisting of gefarnate, aceglutamide aluminum, sucralfate, L-glutamine, sofalcone, teprenone, plaunotol, rebamipide, aldioxa, cetraxate and troxipide in the nasally administrable composition according to claim 1.

9. A method of treating a patient with a physiologically active peptide comprising nasally administering to a patient in need thereof, a composition according to claim 1.

* * * * *